United States Patent
Palpu et al.

(10) Patent No.: US 7,438,932 B2
(45) Date of Patent: *Oct. 21, 2008

(54) METHOD FOR TREATING STOMACH ULCERS WITH HERBAL EXTRACT COMPOSITION

(75) Inventors: Pushpangadan Palpu, Utter Pradesh (IN); Rao Chandana Venkateswara, Utter Pradesh (IN); Govindarajan Raghavan, Uttar Pradesh (IN); Mehrotra Shanta, Uttar Pradesh (IN); Radhakrishnan Krishnan Nair, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 11/216,070

(22) Filed: Sep. 1, 2005

(65) Prior Publication Data

US 2005/0287235 A1 Dec. 29, 2005

Related U.S. Application Data

(62) Division of application No. 10/383,239, filed on Mar. 7, 2003, now Pat. No. 7,025,995.

(30) Foreign Application Priority Data

Dec. 19, 2002 (WO) ........................ PCT/IB02/05518

(51) Int. Cl.
*A61K 36/8965* (2006.01)
*A61K 36/235* (2006.01)
*A61K 36/00* (2006.01)

(52) U.S. Cl. ..................................... 424/725

(58) Field of Classification Search ........................ None
See application file for complete search history.

(56) References Cited

U.S. PATENT DOCUMENTS

| | | | | |
|---|---|---|---|---|
| 5,411,733 | A | * | 5/1995 | Hozumi et al. ............... 424/727 |
| 5,595,756 | A | * | 1/1997 | Bally et al. .................. 424/450 |
| 5,693,327 | A | * | 12/1997 | Shah .......................... 424/734 |
| 5,728,384 | A | | 3/1998 | Tokuyama |
| 6,187,313 | B1 | | 2/2001 | Segelman |
| 6,218,183 | B1 | * | 4/2001 | Kumar et al. ............... 435/420 |

OTHER PUBLICATIONS

Revilla et al. Comparison of Several Procedures Used for the Extraction of Anthocynains From Red Grapes; J. Agric. Food Chem. 1998, 46, pp. 4592-4597.*
Phillipson, J. New Drugs From Nature—It Could be Yew; Phytotherapy Research 13 (1999) pp. 2-8.*
Gura, T.: Systems for Identifying New Drugs are Often Faulty; Science, vol. 278 (Nov. 1997) pp. 1041-1042.*
Sairam et al., "Antiulcerogenic Effect of Methanolic Extract of Emblica Officinalis: An Experimental Study," Journal of Ethnopharmacology, Elsevier, vol. 82, 2002, pp. 1-9.
Sairam et al., Prophylactic and Curative Effects of Bacopa Monniera in Gastric Ulcer Models, Phytomedicine, Urban & Fisher Verlag, vol. 8, No. 6, 2001, pp. 423-430.
Rao et al., "Experimental Evaluation of Bocopa Monniera on Rat Gastric Ulceration and Secretion," Indian Journal Physiol Pharmacol, vol. 44, No. 4, 2000, pp. 435-441.
Anonymous, Indian Pharmacopoeia, Government of India, Ministry of Health & Family Welfare, vol. II, 1996.

* cited by examiner

*Primary Examiner*—Patricia Leith
(74) *Attorney, Agent, or Firm*—Foley & Lardner LLP

(57) ABSTRACT

The invention provides a method for treating stomach discomfort, stomachache, intestinal discomfort, gastric ulcer, duodenal ulcer or diarrhea by administration of extracts of *Utleria solicifolia, Asparagus racemosus, Foeniculum vulgare*, and *Ficus glomerata*.

2 Claims, No Drawings

METHOD FOR TREATING STOMACH ULCERS WITH HERBAL EXTRACT COMPOSITION

This application is a divisional application of U.S. patent application Ser. No. 10/383,239, filed Mar. 7, 2003, which claims priority to Application PCT/IB02/05518, filed Dec. 19, 2002.

TECHNICAL FIELD

The present invention relates to development of an antiulcer herbal composition(s), process of preparing the extracts useful for preparing herbal formulation to treat ulcers.

BACKGROUND ART

Peptic ulcer represents a major health problem, both in terms of morbidity and mortality. Research advances during the last decade have offered new insights in the therapy and prevention of gastroduodenal ulceration by measures directed at strengthening the mucosal defense system rather than by attenuating the aggressive acid-pepsin factors held responsible for the induction of ulcers. The rise in gastric acidity and peptic activity are usually a manifestation of a physiological disturbance affecting one or more mechanisms which normally regulate gastric secretion. Neurotransmitters or hormones that directly stimulate secretion of hydrochloric acid and pepsin by the gastric glands are acetylcholine, gastrin and histamine. In addition there are other factors which play an important role in the manifestation of peptic ulcers. Activity of the gastric secretary cells has been found to be stimulated by caffeine, alcohol, hydrochloric acid, sodium chloride, non steroidal anti-inflammatory drugs (NSAIDS) and stress.

The recent daily life is called a stress age and the chances of receiving stress have been increased by the kaleidoscopic change of the living environment and the increase of the complexity of personal relations. Also, the chance of taking many virtual, which do not exist in nature has been increased.

Thus, the number of persons suffering from a stomach ulcer, a duodenal ulcer, etc., by these factors has been increased and various antiulcer agents have been developed and utilized at present. The antiulcer agents which have been used at present are largely classified into a digestive power depressant, a gastric juice secretion depressant, a mucous membrane protective tissue reparative agent, etc., and are orally or subcutaneously administered. However, these preparations are isolated medicaments or synthesized medicaments, each medicament has each side effects, whereby the restrictions about the applicable objects and the using amount become severe, and an effective and safe antiulcer agent has not yet been developed and utilized.

Thus, since these conventional antiulcer agents can not be regularly used from the point of the safety, they can not be utilized for the prophylaxis and the recurrence prevention. On the other hand, as preventives for ulcer, medicines for intestinal disorders and medicaments having the secretion preventing effect of gastric juice only are used and hence, they are not said to be preventives for a ulcer in true meaning. At present, side effects of medicaments to a human being become a problem and hence the development of a medicament having an antiulcer effect, which is a natural product, gives no side effects, and is sufficiently safe even when the medicament is regularly used as a preventive or a recurring preventing agent has been required.

Hitherto only on oral tradition of Malasar and Kadar tribes of Kerala use *Utleria solifolia* for treatment of intestinal ailments like colic and bleeding in stomach. The synthetic conventional drugs either inhibit acid secretion or cure the ulcer. The long term treatment of the present synthetic drugs completely inhibits the acid and pepsin secretion which is normally responsible for digestion and function of stomach and causes cancer. The offensive acid, pepsin and defensive mucin of the stomach plays a critical role in stomach function. The *Helicobacter pylori* bacteria, offensive acid, pepsin, consumption of hot food disrupts the continuity of the cells and leads to ulcer and gastric cancer, yet there is no complete cure. Therefore for the treatment of acute gastric/duodenal ulcer, and *H. pylori*, a novel herbal formulation is required. Accordingly studies were undertaken to develop a oral formulation containing herbal drugs along with additives for oral ingestion to treat acute gastric/duodenal ulcer and also to treat internal bleeding.

OBJECTS OF THE INVENTION

The main object of the present invention to provide a novel anti-ulcer herbal formulation useful for the treatment of acute and chronic ulcers of stomach and duodenum.

Another objective of the present invention is to prepare herbal formulation(s) that gives immediate relieves the acidity of the stomach by neutralizing the excess acid.

Yet another object of the present invention is to prepare herbal formulation(s) with a combination of the plants which are used in diarrhea, intestinal discomforts and antimicrobial.

SUMMARY OF THE INVENTION

Accordingly, the present invention provides a herbal formulation useful in the treatment of acute and chronic ulcers in stomach. The herbal formulation comprising of *Utleria solifolia* that has been used by Malasar and Kadar tribes, Kerala as mentioned in prior art for the above mentioned purpose as the active ingredient. Along with this plants used traditionally like *Asparagus racemosus, Foeniculum vulgare*, and *Ficus glomerata* are added which are used in intestinal discomforts and as an galactogogue together with conventional additives.

DETAILED DESCRIPTION OF THE INVENTION

Accordingly, the present invention provides a novel anti-ulcer herbal synergistic formulation useful for the treatment of acute and chronic ulcers of stomach and duodenum, said formulation comprising:

a) 50% aqueous alcoholic extracts of the plants comprising *Utlaria solicifolia* 2-5 wt. %, *Asparagus racemosus* 1-3 wt. %, *Foeniculum vulgare* 2-4 wt. %, and *Ficus glomerata* 3-5 wt. % in an oral dosage form selected from a group consisting of a tablet, a capsule, a powder and a liquid.

The novelty of the present investigation is (1) herbal formulation for the treatment of gastric and duodenal ulcers (2) the herbal formulation neutralizes the excess acid in the stomach (3) the herbal formulation is useful in healing and curing of ulcers (4) unlike the commercial antiulcer agents, the herbal formulation also checks the internal bleeding.

In an embodiment, the plant extracts used may be *Utlaria solicifolia, Asparagus racemosus, Foeniculum vulgare*, and *Ficus glomerata*.

In still another embodiment, the formulation may be made into tablet, capsule or powder ready for suspension.

In yet another embodiment, the binder used may be either starch or gum acacia or carboxymethyl cellulose In still another embodiment, the diluent used to make up the dosage form may be lactose.

In another embodiment, the extracts of plants used are 50% aqueous alcoholic extracts.

In another embodiment, alcohol used is ethanol.

In still another embodiment, formulation(s) treats stomach discomforts, gastric cancer, stomachache, intestinal discomforts, gastric and duodenal ulcers.

In yet another embodiment, the extracts of the plants are mixed in the ratio *Utlaria solicifolia* 2-5 wt. %, *Asparagus racemosus* 1-3 wt. %, *Foeniculum vulgare* 2-4 wt. %, and *Ficus glomerata* 3-5 wt. % along with conventional additives to form oral solid dosage forms.

In another embodiment, formulation(s) comprises about 8-17% wt of the total formulation.

In still another embodiment, extract of *Utlaria solicifolia* is a rhizome extract.

In yet another embodiment, the plant extracts are obtained: from plant parts selected from leaf, rhizome and aerial parts.

In still another embodiment, the lubricants used are from starch and lactose.

In an embodiment, the formulation is used in treating diarrhea, intestinal discomforts and is an antimicrobial agent.

In another embodiment, the formulation immediately relieves the acidity of the stomach by neutralizing the excess acid.

In another embodiment, the formulation at a dose of 100 to 200 mg/kg in cold restraint stress induced ulcers gives an ulcer index of 11.2±3.1 to 4.2±1.0

In yet another embodiment, the formulation at a dose of 100 to 200 mg/kg in cold restraint stress induced ulcers gives an % curative ratio of 83.59 to 56.25.

In still another embodiment, the formulation at a dose of 100 to 200 mg/kg in pylorus ligation induced ulcers gives an ulcer index of 6.1±0.8 to 4.8±1.2.

In another embodiment, the formulation at a dose of 100 to 200 mg/kg in pylorus ligation induced ulcers gives an % curative ratio of 57.93 to 66.90.

In yet another embodiment, the formulation at a dose of 100 to 200 mg/kg showed lipid peroxidation capacity in rat gastric mucosa of 0.1±0.01 to 0.21±0.01.

In still another embodiment, the formulation at a dose of 100 to 200 mg/kg in ethanol induced changes in gastric ulcers of 64.94 to 86.75% protection and significant increase in gastric wall mucus in rats.

In yet another embodiment, the formulation at a dose of 100 to 200 mg/kg in aspirin induced changes in gastric ulcers in rats showed an ulcer index of 7.1±2.2 to 6.2±1.3 and % curative ratio of 61.41 to 66.30.

In still another embodiment, the formulation at a dose of 100 to 200 mg/kg in acetic acid induced (ulcer healing) chronic ulcers in rats showed 2.1 to 0.0% incidence of perforations and 31.2 in control.

As a result of intensive study conducted by the inventors with the aim of achieving aforementioned objectives, new formulations for oral ingestion were developed employing herbal drugs which are from natural origin, incorporating them into binders and diluents to form oral dosage forms.

Accordingly, the present investigation deals with the oral dosage form formulation(s). Each formulation has been described in detail giving the formula of the ingredients along with the method of preparation. These examples are for illustration only and should not be construed to limit the scope of the invention.

The first step in the preparation of these formulations involves a process for making, the plant material suitable for formulating into a tablet/capsule. The specified portion of the plant is collected and dried under shade at room temperature (25-35° C.) for 72 hours or until the material gets dried. The material is then powdered into a fine powdered. A specified amount of the powdered material is then extracted exhaustively with 50% aqueous alcohol at room temperature (25-35° C.). Extraction was carried out in a closed container immersing specified amount of the plant material in specified solvent (1:8-1:15 ratio) for 4-7 days. At the end of this stage, solvent is decanted and filtered if necessary to make it free from plant debris. The solvent is then concentrated by evaporating under vacuum at less than 40-60° C. The concentrate is then freeze dried to obtain final product in powder form. The final product is then made into oral dosage form by using it as an ingredient for making tablets and capsules. Suitable binders like starch and diluents like lactose are added to make up the formulation.

EXAMPLE-1

| | |
|---|---|
| *Utlaria solicfolia* | 3 wt. % |
| *Asparagus racemosus* | 2 wt. % |
| *Foeniculum vulgare* | 3 wt. % |
| *Ficus glomerata* | 3 wt. % |
| Starch paste | 15 wt. % |
| Talc | 1 wt. % |
| Lactose | q.s. to make 100% |

*Utlaria solicifolia, Asparagus racemosus, Foeniculum vulgare, Ficus glomerata* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilized to obtain the extract in powder form.

15 g of starch is mixed with water and heated to form a paste. The weighed quantities of the plant extracts are then blended with starch paste and then lactose is added quantity sufficient to make 100 g. The ingredients are then mixed properly with the starch paste to form a mass. The mass is then granulated in a granulator and then the dry at 104° F. and screen through 16 mesh screen. Talc is added to the dried granules and then they are punched in the tablet-punching machine to form uniform tablets.

The formulation is useful for the treatment of acute and chronic gastric and duodenal ulcers and internal bleeding

EXAMPLE-2

| | |
|---|---|
| *Utlaria solicifolia* | 2 wt. % |
| *Asparagus racemosus* | 1 wt. % |
| *Foeniculum vulgare* | 4 wt. % |
| *Ficus glomerata* | 4 wt. % |
| Lactose | q.s to make 100% |

*Utlaria solicifolia, Asparagus racemosus, Foeniculum vulgare, Ficus glomerata* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilized to obtain the extract in powder form. The weighed quantities of the plant extracts as mentioned are mixed with the diluent lactose and then are filled in hard gelatin capsules and are dispensed.

The formulation is useful for the treatment of acute and chronic gastric and duodenal ulcers and internal bleeding Procedures for antiulcer activity screening:

1. Ethanol induced ulcers: The gastric ulcers were induced in rats by administering ethanol (1 ml/200 g, 1 h) and the animals were sacrificed by cervical dislocation and stomach was incised along the greater curvature and examined for ulcers.
2. Aspirin induced ulcers: Aspirin in dose of 200 mg/kg was administered to the animals and ulcers were scored after 4 hours. The stomach was taken out and cut open along with greater curvature and the ulcers were scored by a person unaware of experimental protocol in the glandular portion of the stomach.
3. Cold restraint stress—induced ulcers: Rats were strapped on a wooden plank and kept them at 4-6° C. for 2 hours. The animals were then sacrificed by cervical dislocation and ulcers were scored on the dissected stomach.
4. Pylorus ligated induced ulcers: Animals were anaesthetized using pentobarbitione (35 mg/kg, i.p.), the abdomen was opened and pylorus ligation was done without causing any damage to its blood supply. The stomach was replaced carefully and the abdomen wall was closed in 2 layers with interrupted sutures. The animals were deprived of water during postoperative period. After 4 hours stomach were dissected out and contents were collected and ulcer index was calculated.
5. Acetic acid induced ulcers: The rats were anaesthetized with pentobarbitone (35 mg/kg, i.p.). The abdomen was opened and the stomach was visualized. Cylindrical glass tube of 6 mm diameter was tightly placed upon the anterior serosal surface of the glandular portion on the stomach 1 cm away from the pyloric end. 50% acetic acid (0.06 ml/animal) was instilled into the tube and allowed to remain 60 s on the gastric wall. After removal of the acid solution, the abdomen was closed in 2 layers and animals were caged and fed normally. The animals were sacrificed after the last dose of treatment either on $6^{th}$ or $11^{th}$ of day of experiment to assess the ulcer size healing. Ulcer index was calculated based upon the product of length and width ($mm^2$/rat) of ulcers.
6. Cysteamine induced duodenal ulcers: Cysteamine in 2 doses of 400 mg/Kg of 4 intervals time were administered to induce duodenal ulcers. The animals were sacrificed after drug treatment and observed for the presence or absence of ulcers.

TABLE 1

Effect of antiulcer Herbal composition ($HC_1$) and formulation without *Utlaria solicifolia* ($HC_2$) on cold restraint stress (CRS) and pylorus ligation (PL) - induced changes in gastric ulcers in rats.

| | | CRS - induced ulcers | | PL - induced ulcers | |
|---|---|---|---|---|---|
| Treatment | Dose | Ulcer Index | % Curative Ratio | Ulcer Index | % Curative Ratio |
| Control | — | 25.6 ± 4.2 | — | 14.5 ± 2.5 | — |
| $HC_1$ | 100 | 11.2 ± 3.1[a] | 56.25 | 6.1 ± 0.8[b] | 57.93 |
| $HC_1$ | 200 | 4.2 ± 1.0[c] | 83.59 | 4.8 ± 1.2[b] | 66.90 |
| $HC_2$ | 100 | 17.2 ± 3.1 | 32.81 | 10.5 ± 2.8 | 27.59 |
| $HC_2$ | 200 | 13.3 ± 4.5 | 48.05 | 7.8 ± 1.6[a] | 46.21 |
| Ranitidine | 50 | 5.2 ± 1.1[c] | 79.68 | 5.1 ± 1.3[b] | 64.82 |

Values are mean ± SEM for six rats.
P:
[a] <0.05,
[b] <0.01 and
[c] <0.001 compared to respective control group.
NOTE:
No mortality was found in any of the treated group.
No gross abnormality in behavior was observed in the animal exposed with $HC_1$ herbal preparation.

$HC_1$ showed dose dependent and significant (P:[a]<0.05 to P:[a]<0.001) ulcer protective effect ranged 56.25-83.59%. The $H_2$ receptor blocker ranitidine showed significant protection and % protection (64.82 and 79.68%) in CRS and pylorus ligation induced ulcers.

EXAMPLE-3

| | |
|---|---|
| *Utlaria solicifolia* | 4 wt. % |
| *Asparagus racemosus* | 2 wt. % |
| *Foeniculum vulgare* | 3 wt. % |
| *Ficus glomerata* | 3 wt. % |
| Sodium bicarbonate | 0.5 wt. % |
| Citric acid | 0.5 wt. % |
| Lactose | q.s to make 100% |

*Utlaria solicifolia, Asparagus racemosus, Foeniculum vulgare, Ficus glomerata* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilized to obtain the extract in powder form. The extracts of the plants are mixed with sodium bicarbonate, and citric acid. It is then dry granulated, sieved and punched to form effervescent tablets. The formulation is useful for the treatment of acute and chronic gastric and duodenal ulcers and internal bleeding

EXAMPLE-4

| | |
|---|---|
| *Asparagus racemosus* | 2 wt. % |
| *Foeniculum vulgare* | 4 wt. % |
| *Ficus glomerata* | 4 wt. % |
| Starch paste | 15 wt. % |
| Talc | 1.5 wt. % |
| Lactose | q.s. to make 100% |

*Asparagus racemosus, Foeniculum vulgare, Ficus glomerata* were collected and dried in shade. The dried material (1 Kg) is then powdered and extracted with 50% aqueous alcohol (3 L) for 5 days. At the end of this, the solvent is decanted and filtered if necessary to remove the plant debris. The extract is then concentrated under vacuum at less than 50° C. Then the extract is lyophilized to obtain the extract in powder form.

15 g of starch is mixed with water and heated to form a paste. The weighed quantities of the plant extracts are then blended with starch paste and then lactose is added quantity sufficient to make 100 g. The ingredients are then mixed properly with the starch paste to form a mass. The mass is then granulated in a granulator and then the dry at 104° F. and 1 screen through 16-mesh screen. Talc is added to the dried granules and then they are punched in the tablet-punching machine to form uniform tablets.

The formulation is useful for the treatment of acute ulcers.

In case of HC2 formulation (without *Ulteria solicifolia*) the significant (P<0.05) ulcer protection observed at 200 mg/Kg in Pylorus induced ulcers only.

ADVANTAGES

1. Neutralizes the excess acid in the stomach.
2. Used in acute and chronic gastric/duodenal ulcers.
3. Used in healing and curing of ulcers.
4. Useful in curing internal bleeding.

REFERENCES CITED

| U.S. patents | | |
|---|---|---|
| 6,187,313 | February, 2001 | Segelman |
| 5,728,384 | March, 1998 | Tokuyama |

Other documents

Sairam et al. J. Ethnopharmacology. 82 pp. 1-9, 2002.
Sairam et al. Phytomedicine, 86 (6), pp. 423-430, 2001.
Raw et al. Indian J. Physiol. Pharmacol, 44(4), pp. 435-441, 2000.
Remington, The science and practice of pharmacy, $19^{th}$ edition, Vol II. pp. 1635, 1995
Anonymous. Indian Pharmacopoeia. Govt of India, 1996.

The invention claimed is:

1. A method of treating stomach discomfort, stomachache, intestinal discomfort, gastric ulcer, duodenal ulcer or diarrhea comprising administering to a patient in need thereof an effective amount of an herbal formulation comprising a) 2 to 5% of an extract of *Ulteria salicifolia* b) 1 to 3% of an extract of *Asparagus racemosus* c) 2 to 4% of an extract of *Foeniculum vulgare* d) 3 to 5% of an extract of *Ficus glomerata* and e) 83 to 92% of a pharmaceutically acceptable excipient, wherein said extracts of (a), (b), (c) and (d) are obtained by alcoholic or 50% aqueous alcoholic extraction and wherein said percentages are weight percentages in the total weight of the herbal formulation.

2. The method of claim 1, wherein the herbal formulation composition is administered at a dose of 100 to 200 mg/kg.

* * * * *